(12) United States Patent
Shen (10) Patent No.: US 7,021,822 B2
(45) Date of Patent: Apr. 4, 2006

(54) COATING DRY ESTIMATING METHOD, COATING DRY ESTIMATING SYSTEM AND RECORDING MEDIUM

(75) Inventor: Jianrong Shen, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/733,379

(22) Filed: Dec. 12, 2003

(65) Prior Publication Data

US 2005/0047476 A1    Mar. 3, 2005

(30) Foreign Application Priority Data

Dec. 13, 2002    (JP)    .............. 2002-362428

(51) Int. Cl.
*G01N 25/00*    (2006.01)
*F26B 25/22*    (2006.01)
(52) U.S. Cl. .............. 374/53; 374/102; 703/2; 34/270
(58) Field of Classification Search .............. 374/53, 374/102; 34/491, 270; 118/666
See application file for complete search history.

(56) References Cited

U.S. PATENT DOCUMENTS

| | | | | |
|---|---|---|---|---|
| 4,589,072 A | * | 5/1986 | Arimatsu ............... | 374/53 |
| 4,907,533 A | * | 3/1990 | Nelson et al. ........... | 34/270 |
| 5,136,497 A | * | 8/1992 | Coe et al. ............... | 703/2 |
| 5,345,397 A | * | 9/1994 | Handel et al. ........... | 700/274 |
| 6,099,162 A | * | 8/2000 | Walsh .................... | 374/53 |
| 6,711,531 B1 | * | 3/2004 | Tanaka et al. .......... | 703/6 |
| 6,885,964 B1 | * | 4/2005 | Ogino et al. ........... | 702/136 |

FOREIGN PATENT DOCUMENTS

| | | |
|---|---|---|
| DE | 43 16 784 A1 | 11/1994 |
| EP | 0 367 020 A1 | 5/1990 |
| EP | 0 681 123 A2 | 11/1995 |
| JP | 3-96760 | 4/1991 |
| JP | 06-238221 | 8/1994 |
| JP | 2001-096216 | 4/2001 |

OTHER PUBLICATIONS

European Search Report dated Jun. 29, 2004.

* cited by examiner

*Primary Examiner*—Diego Gutierrez
*Assistant Examiner*—Stanley J. Pruchnic, Jr.
(74) *Attorney, Agent, or Firm*—McGinn IP Law Group, PLLC (57) ABSTRACT

Temperature data representing transition of a temperature distribution of a coating target with time lapse is calculated. Subsequently, the integrated value of the amount of heat applied to the coating is calculated on the basis of the temperature data. The dry state of the coating is estimated on the basis of the integrated value of the heat amount. In order to estimate the dry state of the coating, the integrated value of the amount of heat applied to the coating and the threshold values for the dry judgment of the coating are compared with each other.

20 Claims, 7 Drawing Sheets

COATING DRY ESTIMATING METHOD, COATING DRY ESTIMATING SYSTEM AND RECORDING MEDIUM

BACKGROUND OF THE INVENTION

1. Field of the Invention

The present invention relates to a coating dry estimating method of estimating a dry state of coating applied to a coating target, a coating dry estimating system and a recording medium.

2. Description of the Related Art

Dry of coating applied to a coating target such as a vehicle body or the like is carried out by radiation based on infrared rays or the like or by high temperature air blowing. The drying process of the coating contains not only evaporation of solvent contained in the coated film, but also hardening of coated film. The hardening of the coated film progresses by inducing bridging reaction (polymerization reaction) of molecules of coating material contained in the coated film to polymerize the molecules. In the hardening reaction of the coated film (coating) as described above, a proper dry temperature range and a proper integrated heat amount range exist every coating material. In a drying furnace, the surface temperature is different among sites of the coating target, and thus dispersion occurs in the dry state of the coating every site. Therefore, when the dry state of the coating is estimated, it is particularly important to estimate the dry state of a site which is hardly dried like the inside of a car body or the like. In order to excellently dry the coating over the coating target, it is required to optimize the setting of dry conditions in the drying furnace, the body structure of the coating target, the coating conditions, etc. so that the dispersion of the dry state is eliminated.

For example, a coating drying furnace simulation system for analyzing the temperature distribution in the drying furnace as disclosed in JP-A-6-238221 is known as a system for estimating the temperature in the drying furnace in the dry process of a coating target. Furthermore, JP-A-2001-96216 discloses a baking temperature monitoring system for monitoring the surface temperature of a coating target in a drying furnace.

However, in the system described in JP-A-6-238221, the temperature in the drying furnace is analyzed, however, no analysis is carried out on the surface temperature of the coating target and the dry state of the coating. In order to estimate the dry state of the actual coating target (actual work) with high precision, it is preferable to make an analysis not on a drying-furnace basis, but on a coating-target basis.

The present invention has been implemented in view of the foregoing situation, and has an object to estimate the dry state of the coating target with high precision.

SUMMARY OF THE INVENTION

The present invention has been implemented in view of the foregoing situation, and has an object to estimate the dry state of the coating target with high precision.

In order to solve this problem, a first invention provides a coating dry estimating method of estimating a dry state of coating on a coating target. This method has a first step of calculating temperature data indicating transition of a temperature distribution of the coating target with time lapse, a second step of calculating an integrated value of an amount of heat applied to the coating on the basis of the temperature data, and a third step of estimating the dry state of the coating on the basis of the integrated value of the amount of heat.

Here, in the first invention, it is preferable that the third step contains a step of comparing the integrated value of the amount of heat applied to the coating with a threshold value for judging dry of the coating to estimate the dry state of the coating. In this case, it is also preferable that the second step is a step of determining a time period for which the temperature of the coating target is within a predetermined temperature range in the temperature data, and calculating the integrated value of the amount of heat applied to the coating within the time period. And this second step may contain a step of correcting the integrated value of the amount of heat on the basis of at least one of the film thickness of the coating, the kind of coating material used for the coating and the content of solvent contained in the coating.

In the first invention, it is preferable that the first step contains a step of superposing a coating target mesh achieved by representing the coating target in the form of a mesh on an in-furnace area mesh achieved by modeling a dry furnace and representing the dry furnace in the form of a mesh while moving the coating target mesh in conformity with a movement pattern representing a movement locus of the coating target, thereby generating superposed grids time-sequentially, and a step of analyzing the temperature distribution of the coating target by using each of the superposed grids generated time-sequentially. And, it is also preferable that the coating target mesh comprises a fine mesh achieved by representing the internal structure of a member at a note site to be noted for analysis in the form of a mesh, and a rough mesh achieved by representing the surface of the coating target at portions other than the note site in the form of a mesh.

A second invention provides a recording medium recorded with a program for making a computer execute a coating dry estimating method of estimating a dry state of coating on a coated coating target which is provided in the above first invention.

A third invention provides a coating dry estimating system for estimating a dry state of coating on a coated coating target. This system has a storage device for storing a threshold value for judgment of dry of the coating, and a computer for calculating temperature data representing transition of a temperature distribution of the coating target with time lapse, calculating an integrated value of the amount of heat applied to the coating on the basis of the temperature data, and comparing the integrated value of the amount of heat applied to the coating with the threshold value to estimate the dry state of the coating. It is preferable that the computer calculates a time period for which the temperature of the coating target is within a predetermined temperature range in the temperature data, and calculating an integrated value of the amount of heat applied to the coating within the time period. And it is also preferable that the computer corrects the integrated value of the amount of heat on the basis of at least one of the film thickness of the coating, the kind of coating material used for the coating and the content of solvent contained in the coating.

DESCRIPTION OF PREFERRED EMBODIMENTS

Figure 1:
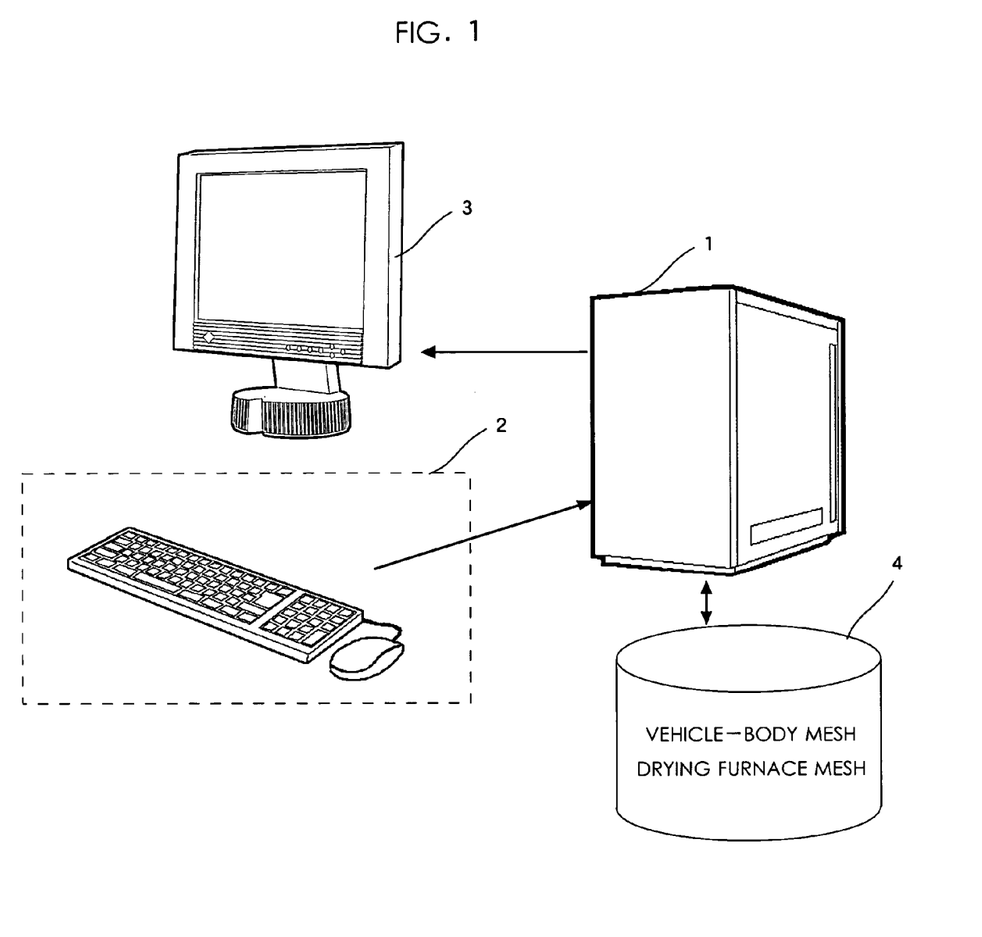
FIG. 1 is a diagram showing a coating dry estimating system.

This embodiment relates to a system for estimating the dry state of coating with time lapse in a drying process for drying coating applied to a vehicle body such as a car or the like while moving the vehicle body in a drying furnace. FIG. 1 is a diagram showing the construction of a coating dry estimating system for vehicle bodies according to the present invention. This system comprises a computer 1, an input device 2 such as a keyboard, a mouse or the like, a display device 3 such as CRT, a liquid crystal display or the like, and a storage device 4 such as a magnetic disc or the like. The computer 1 comprises CPU, RAM, ROM, an input/output interface, etc. as well known. The computer 1 numerically analyzes the surface temperature of a vehicle body serving as an analysis target, and estimates the dry state of the coating on the basis of the analysis result. An operator properly operates the input devic 2 on the basis of the information displayed on the display device 3 to indicate a constituent part serving as an analysis target, input numerical values, etc.

Material characteristic values, dimensions, conditions, etc. associated with the drying furnace, air, the vehicle body and the coating are stored as data for estimating the dry state of the coating in the storage device 4. The data related to the drying furnace contain internal dimension of the drying furnace, a heat source (duct) position, the temperature and velocity of hot air, etc. The data related to the air contain the gas constant, the density, molecular mass, viscosity, heat capacity, thermal conductivity, mass diffusion coefficient, normal state enthalpy, Reynolds number, etc. of the air, etc. The data related to the drying furnace and the data related to the air are used to analyze the temperature distribution in the drying furnace. Furthermore, the data related to the vehicle body contains the density, thermal conductance, heat capacity, electric conductivity, permeability, etc. of the materials constituting the vehicle body. These data related to the vehicle body are used to analyze the temperature distribution on the surface of the vehicle body. Furthermore, the data related to the coating contain a threshold value for the temperature in the drying process of the coating, a threshold value for judgment of the dry of the coating, the type of coating material, the film thickness of the coating, the type of solvent, the content of solvent, specific gravity, coefficient of heat transfer, bridging reaction heat, vaporization heat, etc. These data related to the coating are used to analyze evaporation of the solvent and hardening of the coating. The moving speed of the vehicle body, the treatment time, the initial temperature of the vehicle body, etc. are also stored as analysis conditions for the temperature analysis of the vehicle body in the storage device 4.

Figure 2:
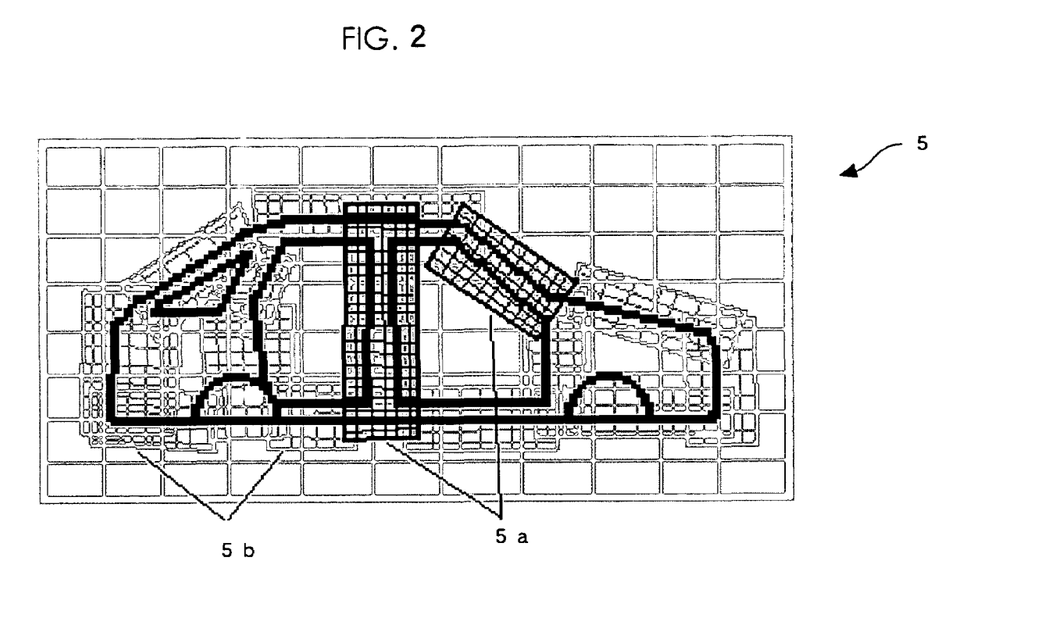
FIG. 2 is a diagram showing an example of a vehicle-body mesh.

The mesh data related to the vehicle body and the drying furnace are stored in the storage device 4. In this embodiment, a vehicle-body mesh 5 (coating target mesh) achieved by representing the coating target in the form of a mesh and a drying furnace mesh 6 are used to calculate the temperature distribution of the overall vehicle body. FIG. 2 is a diagram showing an example of the vehicle body mesh. The vehicle body mesh 5 is achieved by representing the shape of the vehicle body itself and the surrounding space thereof in the form of a mesh. In this embodiment, a front pillar and a center pillar are represented by fine meshes 5a with which the shapes of the sites are finely represented, and the shapes of the other sites are represented by rough meshes 5b with which the shapes of the sites are represented more roughly than those of the fine meshes 5a.

Figure 3:
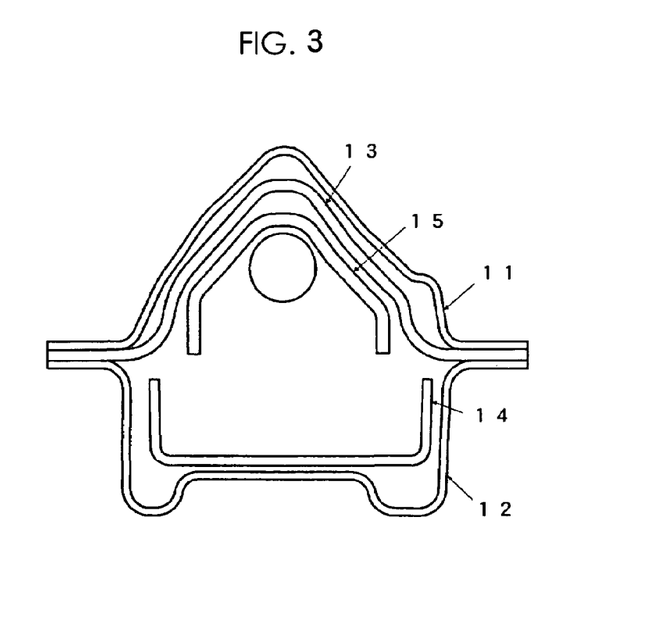
FIG. 3 is a diagram showing a part of the internal structure of a member.

The vehicle-body mesh 5 is generated by superposing two kinds of meshes, a fine mesh 5a and a rough mesh 5b. Here, the fine mesh 5a represents the structure of a site being noted for the coating dry estimation by using a relatively fine mesh. For example, when the front pillar or the center pillar is set as a site being noted, not only the plates 11, 12 corresponding to the outer plates of the vehicle body, but also the internal enforcing members 13 to 15 are finely represented as shown in FIG. 3. The fine mesh 5a is designed in a finer mesh structure than the drying furnace mesh 6 described later from the viewpoint of securing the estimation precision of the coating dry. On the other hand, the rough mesh 5b represents the outer plate of the vehicle body at the portions other than the note sites by using a rougher mesh than the fine mesh 5a, and it does not represent the internal structure. For example, when the front pillar or the center pillar is represented by the rough mesh 5b, only he plates 11, 12 of FIG. 3 are represented by meshes. The reason why the outer plate of the vehicle body at the portions other than the note sites is represented by meshes resides in that the outer plate of the vehicle plate has a great effect on fluidity of air in the drying furnace when the temperature distribution in the drying furnace is determined.

Figure 4:
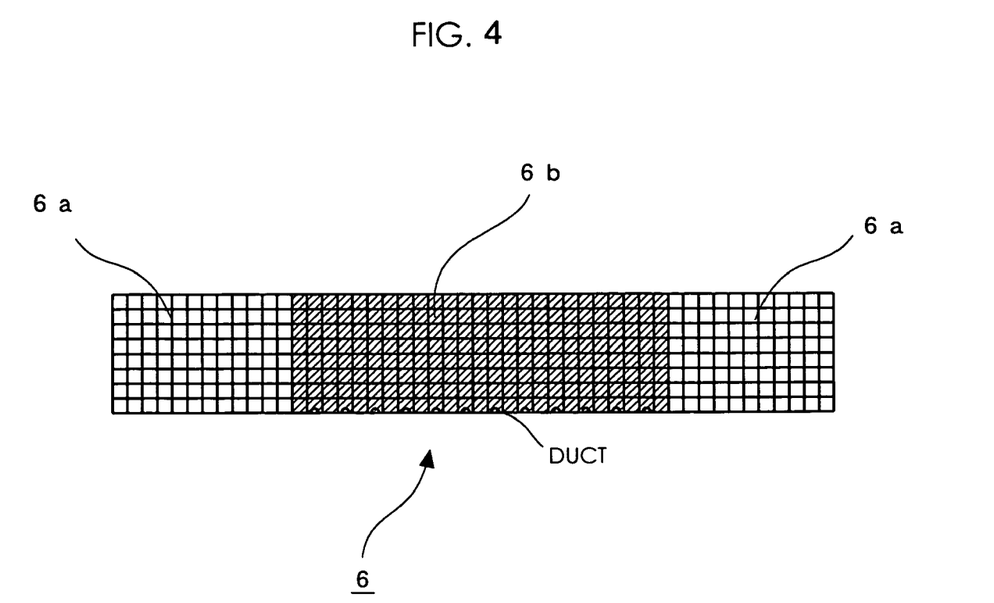
FIG. 4 is a diagram showing an example of a drying furnace mesh.

The drying furnace mesh 6 represents a modeled drying furnace in the form of a mesh. FIG. 4 is a diagram showing an example of the drying furnace mesh 6. That is, an area heated in the drying furnace is represented as an in-furnace area mesh 6b for which the material characteristic value indicating heated air is set. Furthermore, the outside air of the drying furnace is represented as an out-furnace area mesh 6a for which the material characteristic value indicating non-heated air is set. A temperature boundary is set at the boundary between the in-furnace area mesh 6b and the out-furnace area mesh 6a. In addition, a duct, a wall boundary (Wall boundary)of the drying furnace, etc. are further set in the in-furnace area mesh 6a. These meshes 5, 6 are superposed on each other while moving the vehicle-body mesh 5 in conformity with a movement pattern indicating a movement locus of the vehicle body on the drying furnace mesh 6, thereby generating superposed grids time-sequentially.

Figure 5:
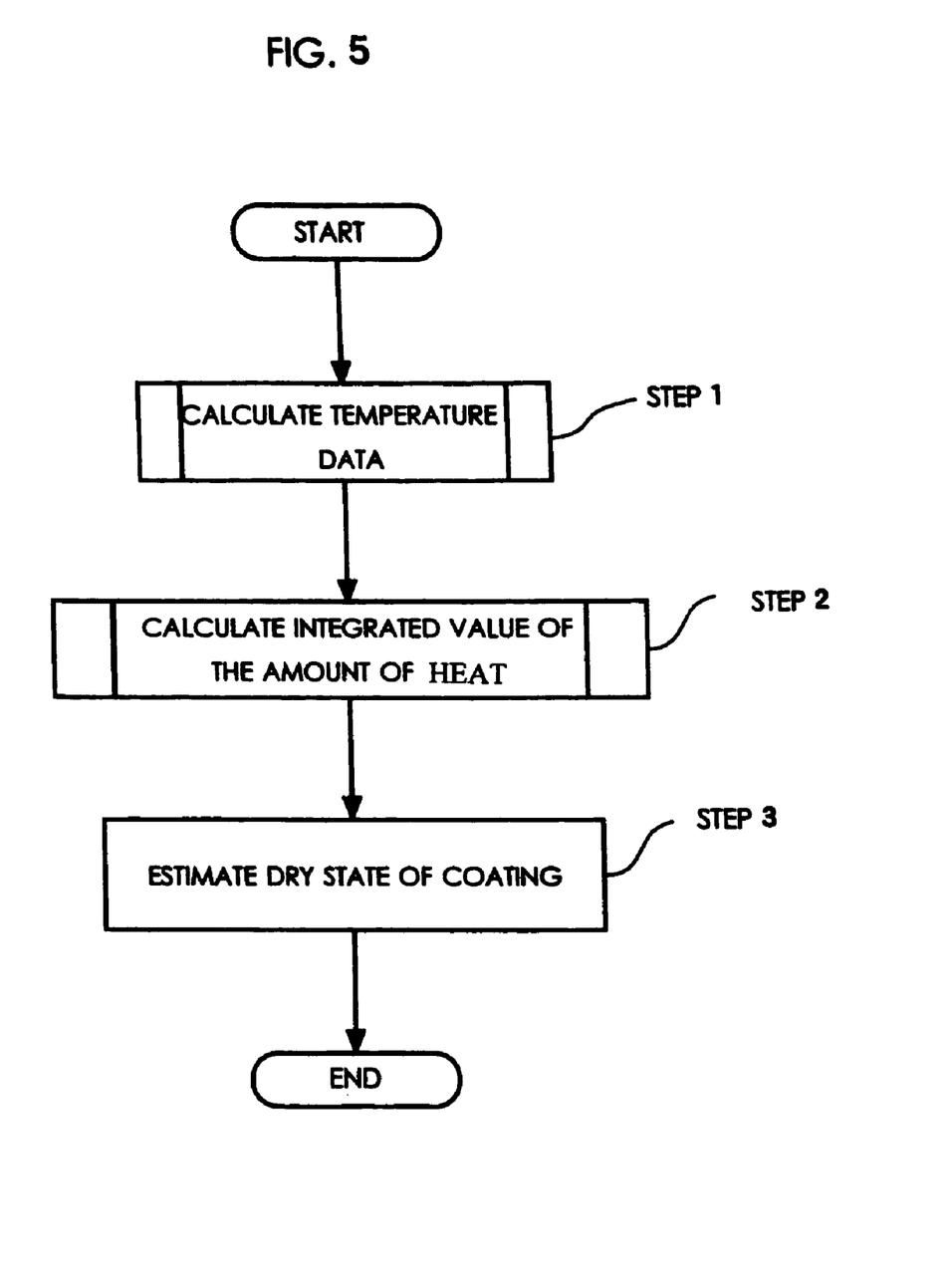
FIG. 5 is a flowchart showing the coating dry state estimating procedure of the vehicle body.
Figure 6:
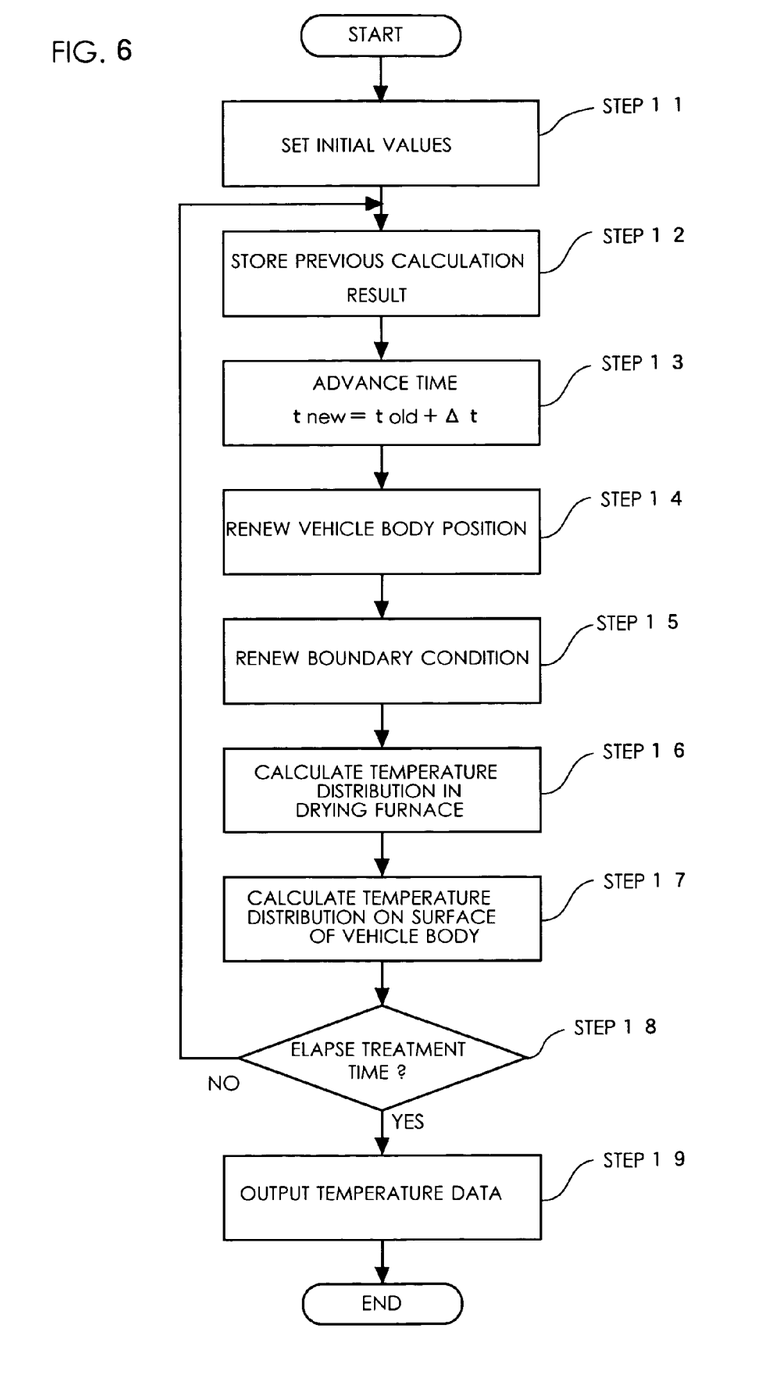
FIG. 6 is a flowchart showing the calculation procedure of temperature data.

FIG. 5 is a flowchart showing the procedure of the coating dry estimation for the vehicle body. In step 1, the computer 1 calculates temperature data representing transition of the temperature distribution of the vehicle body with time lapse. FIG. 6 is a flowchart showing the calculation procedure of the temperature data. First, in step 11, the operator inputs various data such as the superposed grids generated from the vehicle-body mesh 5 and the drying furnace mesh 6, the material characteristic value, the analysis condition, etc. to set the initial values of the temperature distribution for the vehicle body and the drying furnace. Subsequently, in step 12, the computer 1 stores the temperature distribution before calculation (the temperature distribution of the preceding analysis in the second and subsequent analysis) in the storage device 4 such as a magnetic disc or the like. A calculation time step is advanced from a time told for the preceding analysis by Δt [sec] (step 13), the position of the vehicle-body mesh 5 at the current time tnew is renewed, and the vehicle-body mesh 5 is moved ahead along a conveyor line (step 14). After renewing the boundary condition in step 15, the computer 1 solves a well-known thermal diffusion equation by using a finite volume method, a finite element method, a finite differential method or the like to calculate the temperature distribution in the drying furnace (step 16). The temperature distribution on the surface of the vehicle body is calculated on the basis of the temperature distribution in the drying furnace which is calculated in step 16 (step 17). A series of processes from the step 12 to the step 17 as described above are repeated until a predetermined treatment time has elapsed on the basis of a judgment of step 18, whereby the temperature data are achieved as the time-varying temperature distribution. When the predetermined treatment time has elapsed, the step goes from step 18 to step 19, and the computer 1 outputs the temperature data and finishes the calculation processing of the temperature data.

Figure 7:
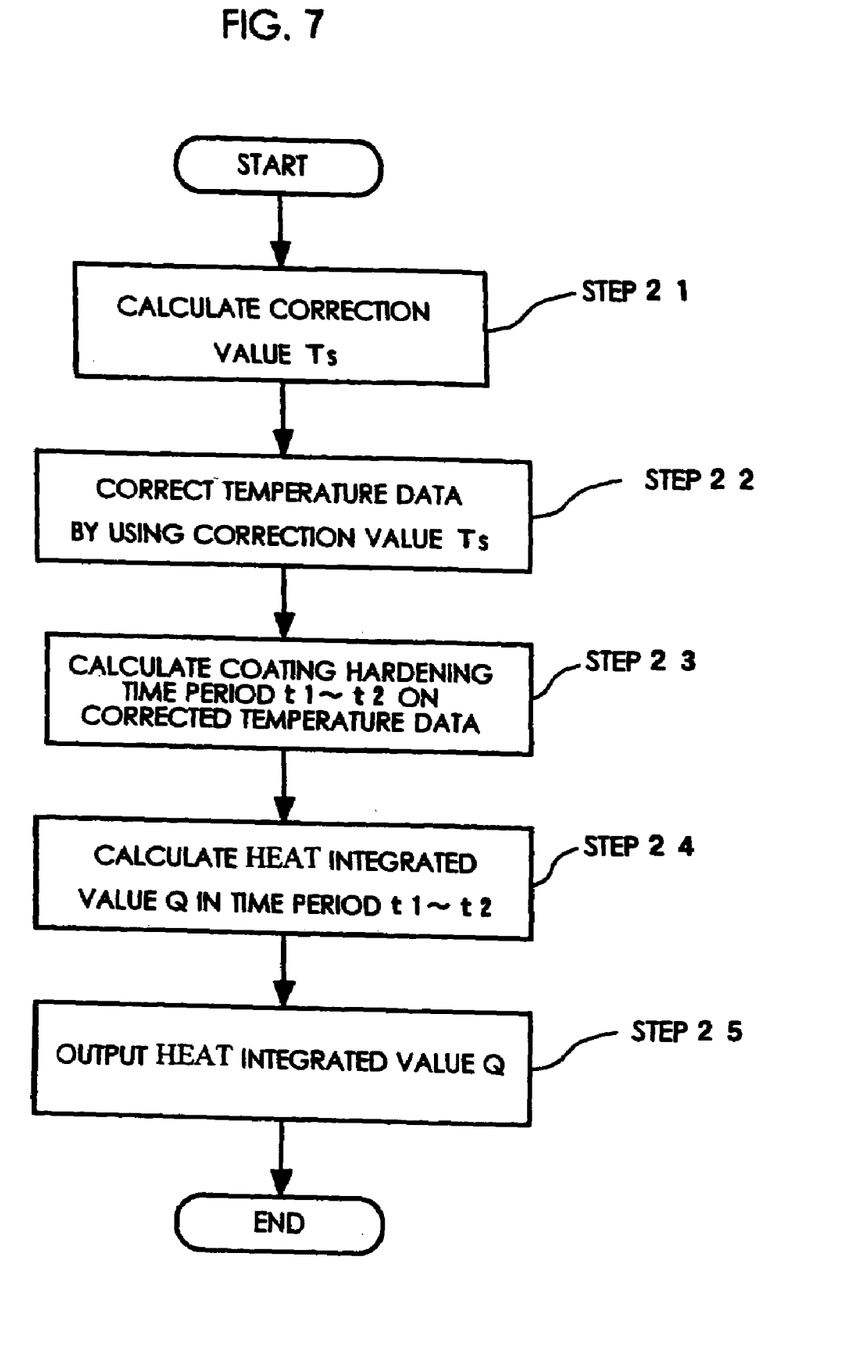
FIG. 7 is a flowchart showing a calculation routine of the integrated value of the amount of heat.
Figure 8:
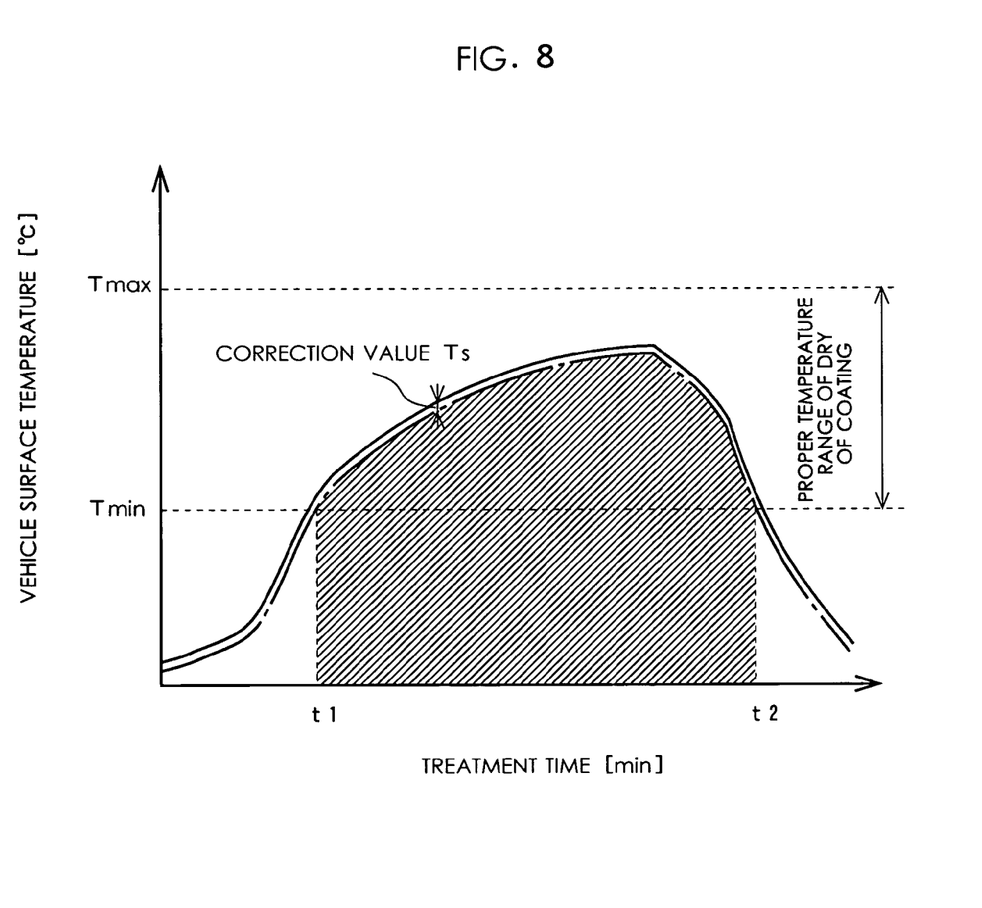
FIG. 8 is a diagram showing the integrated value of the amount of heat.

In step 2 of FIG. 2, the computer 1 calculates the integrated value of the amount of heat (accumulated heat amount) on the basis of the temperature data calculated in the preceding step 1. FIG. 7 shows a calculation routine of the integrated value of the amount of heat, and FIG. 8 is a diagram showing the integrated value of the heat amount. A solid line of FIG. 8 represents transition of temperature at a note site (for example, one mesh in the vehicle-body mesh 5) in the temperature data calculated in the step 1.

First, in step 21, the computer 1 calculates a correction value Ts on the basis of the coating condition. The amount of heat consumed through the dry of the coating is associated with hardening of the coating and evaporation of the solvent. In this case, the correction value Ts for subtracting the heat amount related to the evaporation of the solvent from the temperature data is calculated by the equation 1. The condition of the coating used to calculate the correction value Ts contains the kind of the coating material, the film thickness of the coating, the content of the solvent contained in the coating. In the equation 1, K represents a coefficient based on the type of the coating material, Th represents the film thickness of the coating and C represents the content of the solvent. Furthermore, a1 to a4 represent predetermined coefficients. In this embodiment, three input parameters K, Th, C are used. However, all the parameters are not necessarily used, and at least one of them may be used.

$$Ts = a1 + a2 \times K + a3 \times Th + a4 \times C \qquad \text{[Equation 1]}$$

In step 22, the computer 1 corrects the temperature data by using the correction value Ts. In this embodiment, the correction of the temperature data is carried out by uniformly subtracting the correction value Ts from the temperature data (transition of the temperature) before the correction. A one-dotted chain line of FIG. 8 represents the temperature data corrected on the basis of the correction value Ts.

In step 23, by using the corrected temperature data, the computer 1 calculates a time period for which the hardening of the coating progresses. In general, it is required as a condition for progression of the hardening of the coating that the temperature of the coating is within a proper temperature range in the dry of the coating. The temperature range is varied in accordance with the coating material, and it is regulated by upper and lower threshold values of the upper limit value Tmax of the reaction temperature and the lower limit value Tmin of the reaction temperature. When the temperature of the coating is set to be higher than the upper limit value Tmax of the reaction temperature, a decomposition reaction called as a side reaction occurs in the coating film constituting the coating, and the hardening of the coating film is disturbed. Furthermore, in addition to the decomposition reaction, overheat (excessive dry) of the coating film occurs, and the dry state of the coating becomes bad. On the other hand, when the temperature of the coating is set to be lower than the lower limit value Tmin of the reaction temperature, the bridging reaction for hardening the coating film constituting the coating occurs hardly, and thus the coating is short of dryness. Accordingly, according to this embodiment, the time period from the timing t1 at which the one-dotted chain line (see FIG. 8) representing the corrected temperature data is increased to be larger than the lower limit value Tmin of the reaction temperature till the timing t2 at which the one-dotted chain line is reduced to be less than the lower limit value Tmin of the reaction temperature is calculated as the time period for which the hardening of the coating progresses.

In step 24, the computer 1 calculates the integrated value Q of the amount of heat applied to the coating within the time period from t1 to t2 for which the hardening of the coating progresses. The integrated value Q of the heat amount is calculated by integrating the equation 2 for the corrected temperature data (one-dotted chain line of FIG. 8). In this equation 2, K represents a coefficient based on the kind of the coating material, R represents gas constant, T represents the temperature at some timing of the corrected temperature data, and t1, t2 represents the timing calculated in step 23. The integrated value Q of the heat amount may be calculated on the basis of the corrected temperature data by integrating the amount of heat for the time period from t1 to t2 for which the hardening of the coating progresses. In this case, the integrated value Q of the heat amount corresponds to a hatched portion of FIG. 8. In step 25, the computer 1 outputs the integrated value Q of the heat amount and finishes the calculation processing of the integrated value Q of the heat amount.

$$Q = \int_{t1}^{t2} K e^{\left(-\frac{1}{RT}\right)} dt \qquad \text{[Equation 2]}$$

In step 3 subsequent to step 2, the computer 1 estimates the dry state of the coating. Specifically, the integrated value Q of the amount of heat applied to the coating is compared with the threshold value for the judgment of the dry of the coating, and the dry state of the coating is estimated. The threshold value is set every coating material, and it is regulated by the upper and lower threshold values of the upper limit value Qmax of the integrated value of the heat amount and the lower limit value Qmin of the integrated value of the heat amount. When the integrated value Q of the heat amount is not less than the upper limit value Qmax, a decomposition reaction occurs in the coating film constituting the coating, and also overheat (excessive dry) of the coating film occurs, so that a coating dry failure is judged. On the other hand, if the integrated value Q of the heat amount is not more than the lower limit value Qmin, the hardening reaction does not sufficiently progress, so that it is judged that the dry state of the coating is insufficient. The dry state estimated on the basis of the threshold values and the integrated value Q of the heat amount as described above is calculated for the overall vehicle body by using the superposed grids. The judgment result achieved every vehicle-body site is displayed on the display device 3.

As described above, according to this embodiment, the temperature data and the integrated value of the heat amount are compared with the respective threshold values, whereby the dry state of the coating applied to the vehicle body can be estimated. The operator can grasp the dry state every vehicle-body site by checking the dry state of the coating thus estimated. Accordingly, sites at which coating failure is liable to occur in the vehicle body can be grasped, and coating quality can be enhanced, so that the development time period and the development cost for the improvement in style of vehicle bodies can be reduced. Furthermore, more efficient dry conditions can be set through the estimation and improvement of the dry state of the coating, and thus the present invention contributes to an effect of reducing the exhaust amount of carbon dioxide (energy saving).

Furthermore, in the above embodiment, the calculation of the temperature data representing the time-varying temperature distribution and the calculation of the integrated value of the heat amount (containing the correction related to the solvent) are carried out independently of each other. Accordingly, when the coating conditions such as the kinds of the coating material and the solvent, etc. are changed, the correction related to the coating material and the solvent changed may be carried out by using the temperature data calculated in the preceding analysis. As a result, the calculation of the temperature data can be omitted, and the coating condition can be efficiently selected Furthermore, in this embodiment, the dry estimation of the overall vehicle body is carried out by using the vehicle-body mesh. Therefore, transfer of the heat amount between members of the vehicle body can be calculated, and thus the temperature distribution of the overall vehicle body can be calculated with high precision. Accordingly, the estimation precision of the dry state of the coating can be further enhanced.

In this embodiment, the correction value is subtracted from the temperature data for the correction related to evaporation of solvent. However, the correction method for the evaporation of the solvent is not limited to the above embodiment. For example, it may be modified so that the correction value related to the integrated value of the amount of heat is calculated on the basis of the coating condition described above and then the correction value is subtracted from the integrated value of the heat amount. If the consumption of the heat amount by the evaporation of solvent can be neglected, the correction processing may be omitted. The estimation of the dry state of the coating can be efficiently carried out by selectively carrying out the correction processing on the basis of the coating condition.

A recording medium in which a computer program for implementing the function of the above embodiment is recorded may be equipped to a system having the construction as shown in FIG. 1. In this case, the computer 1 in the system reads out and executes the computer program stored in the recording medium, whereby the object of this invention can be attained. Accordingly, the computer program itself read out from the recording medium implements the novel function of this invention, and thus the recording medium having the program recorded therein constitutes this invention. For example, CD-ROM, a flexible disc, a hard disc, a memory card, an optical disc, DVD-ROM, DVD-RAM or the like may be used as the recording medium in which the computer program is recorded. Furthermore, the computer program itself for implementing the function of the above embodiment has the novel function.

According to this invention, the dry state of coating applied to a coating target is estimated by calculating the integrated value of the amount of heat on the basis of temperature data representing transition of the temperature distribution of the coating target with time lapse. As described above, the estimation of the dry state is carried out on an actual coating-target basis (actual work basis), so that the dry state of the coating target can be estimated with higher precision as compared with the prior art in which the estimation is carried out on a drying-furnace basis.

While the present invention has been disclosed in terms of the preferred embodiments in order to facilitate better understanding of the invention, it should be appreciated that the invention can be embodied in various ways without departing from the principle of the invention. Therefore, the invention should be understood to include all possible embodiments which can be embodied without departing from the principle of the invention set out in the appended claims.

Additionally, the disclosure of Japanese Patent Application No. 2002-362428 filed on Dec. 13, 2002 including the specification, drawing and abstract is incorporated herein by reference in its entirety.

What is claimed is:

1. A coating dry estimating method of estimating a dry state of coating on a coating target, comprising:
   calculating temperature data indicating a transition of a temperature distribution of the coating target with a time lapse;
   calculating an integrated value of an amount of heat applied to the coating on a basis of the temperature data; and
   estimating a dry state of the coating on a basis of the integrated value of the amount of heat.

2. The coating dry estimating method according to claim 1, wherein said estimating comprises comparing the integrated value of the amount of heat applied to the coating with a threshold value to estimate the dry state of the coating.

3. The coating dry estimating method according to claim 2, wherein said calculating an integrated value of an amount of heat comprises:
   determining a time period for which the temperature of the coating target is within a predetermined temperature range in the temperature data; and
   calculating the integrated value of the amount of heat applied to the coating within the time period.

4. The coating dry estimating method according to claim 3, wherein said calculating an integrated value of an amount of heat comprises correcting the integrated value of the amount of heat on a basis of at least one of a film thickness of the coating, a kind of coating material used for the coating, and a content of solvent contained in the coating.

5. The coating dry estimating method according to claim 1, wherein said calculating temperature data comprises:
   superimposing a coating target mesh achieved by representing the coating target in a form of a mesh on an in-furnace area mesh achieved by modeling a dry furnace;
   representing the dry furnace in the form of a mesh while moving the coating target mesh in conformity with a movement pattern representing a movement locus of the coating target, thereby generating superimposed grids time-sequentially, and analyzing the temperature distribution of the coating target by using each of the superimposed grids generated time-sequentially.

6. The coating dry estimating method according to claim 5, wherein the coating target mesh comprises a fine mesh achieved by representing an internal structure of a member at a note site to be noted for analysis in the form of a mesh, and a rough mesh achieved by representing a surface of the coating target at portions other than the note site in the form of a mesh.

7. The coating dry estimating method according to claim 2, wherein said calculating temperature data comprises:
   superimposing a coating target mesh achieved by representing the coating target in a form of a mesh on an in-furnace area mesh achieved by modeling a dry furnace;
   representing the dry furnace in the form of a mesh while moving the coating target mesh in conformity with a movement pattern representing a movement locus of the coating target, thereby generating superimposed grids time-sequentially; and
   analyzing the temperature distribution of the coating target by using each of the superimposed grids generated time-sequentially.

8. The coating dry estimating method according to claim 7, wherein the coating target mesh comprises a fine mesh achieved by representing an internal structure of a member at a note site to be noted for analysis in the form of a mesh, and a rough mesh achieved by representing the surface of the coating target at portions other than the note site in the form of a mesh.

9. The coating dry estimating method according to claim 3, wherein said calculating temperature data comprises:
   superimposing a coating target mesh achieved by representing the coating target in a form of a mesh on an in-furnace area mesh achieved by modeling a dry furnace;
   representing the dry furnace in the form of a mesh while moving the coating target mesh in conformity with a movement pattern representing a movement locus of the coating target, thereby generating superimposed grids time-sequentially; and
   analyzing the temperature distribution of the coating target by using each of the superimposed grids generated time-sequentially.

10. The coating dry estimating method according to claim 9, wherein the coating target mesh comprises a fine mesh achieved by representing an internal structure of a member at a note site to be noted for analysis in the form of a mesh, and a rough mesh achieved by representing a surface of the coating target at portions other than the note site in the form of a mesh.

11. The coating dry estimating method according to claim 4, wherein said calculating temperature data comprises:
   superimposing a coating target mesh achieved by representing the coating target in a form of a mesh on an in-furnace area mesh achieved by modeling a dry furnace;
   representing the dry furnace in the form of a mesh while moving the coating target mesh in conformity with a movement pattern representing a movement locus of the coating target, thereby generating superimposed grids time-sequentially; and
   analyzing the temperature distribution of the coating target by using each of the superimposed grids generated time-sequentially.

12. The coating dry estimating method according to claim 11, wherein the coating target mesh comprises a fine mesh achieved by representing an internal structure of a member at a note site to be noted for analysis in the form of a mesh, and a rough mesh achieved by representing a surface of the coating target at portions other than the note site in the form of a mesh.

13. The method of claim 1, wherein said calculating temperature data comprises superimposing a coating target mesh on an in-furnace mesh.

14. The method of claim 13, wherein said calculating temperature data further comprises moving the coating target mesh relative to the in-furnace mesh.

15. The method of claim 14, wherein said calculating temperature data further comprises analyzing the temperature distribution of the coating target.

16. The method of claim 1, wherein said calculating an integrated value of an amount of heat applied to the coating comprises:
   correcting the temperature distribution of the coating target based upon at least one of a thickness of the coating, a characteristic of a material in the coating, and a content of solvent in the coating to provide a corrected temperature data for the coating; and
   integrating the corrected temperature data for the coating over time to provide the integrated value of the amount of heat applied to the coating.

17. A recording medium recorded with a program for making a computer execute a coating dry estimating method of estimating a dry state of coating on a coated coating target, comprising:
   calculating temperature data indicating transition of a temperature distribution of the coating target with time lapse;
   calculating an integrated value of an amount of heat applied to the coating on a basis of the temperature data; and
   estimating a dry state of the coating on a basis of the integrated value of the amount of heat.

18. A coating dry estimating system for estimating a dry state of coating on a coated coating target, comprising:
   a storage device for storing a threshold value for judgment of a dry state of the coating; and
   a computer for calculating temperature data representing a transition of a temperature distribution of the coating target with time lapse, calculating an integrated value of the amount of heat applied to the coating on a basis of the temperature data, and comparing the integrated value of the amount of heat applied to the coating with the threshold value to estimate a dry state of the coating.

19. The coating dry estimating system according to claim 18, wherein the computer calculates a time period for which the temperature of the coating target is within a predetermined temperature range in the temperature data, and calculating an integrated value of the amount of heat applied to the coating within the time period.

20. The coating dry estimating system according to claim 18, wherein the computer corrects the integrated value of the amount of heat on a basis of at least one of a film thickness of the coating, a kind of coating material used for the coating, and a content of solvent contained in the coating.

* * * * *